United States Patent

Carrozza et al.

Patent Number: 5,449,779
Date of Patent: Sep. 12, 1995

[54] PROCESS FOR PREPARING N,N'-BIS(HYDROCARBYLOXYCARBONYL)-N,N'-BIS(2,2,6,6-TETRAMETHYL-4-PIPERIDYL)DIAMINES

[75] Inventors: Primo Carrozza, Padua; Giovanni Da Roit; Valerio Borzatta, both of Bologna, all of Italy

[73] Assignee: Ciba-Geigy Corporation, Ardsley, N.Y.

[21] Appl. No.: 241,934

[22] Filed: May 11, 1994

Related U.S. Application Data

[63] Continuation of Ser. No. 986,326, Dec. 7, 1992, abandoned.

[30] Foreign Application Priority Data

Dec. 12, 1991 [IT] Italy ................. MI91A3330

[51] Int. Cl.6 .......................... C07D 211/32
[52] U.S. Cl. ..................... 546/189; 546/190
[58] Field of Search .................. 546/189, 190

[56] References Cited

U.S. PATENT DOCUMENTS

| | | |
|---|---|---|
| 4,369,321 | 1/1983 | Cantatore . |
| 4,695,599 | 9/1987 | Cantatore . |
| 4,725,634 | 2/1988 | Ishii et al. ............... 546/190 |
| 5,306,495 | 4/1994 | Cantatore et al. ............ 546/190 |

FOREIGN PATENT DOCUMENTS

| | | |
|---|---|---|
| 0031304 | 7/1981 | European Pat. Off. . |
| 0124486 | 11/1984 | European Pat. Off. . |

Primary Examiner—Johann Richter
Assistant Examiner—John Peabody
Attorney, Agent, or Firm—Luther A. R. Hall

[57] ABSTRACT

A process for preparing a compound of the formula (I)

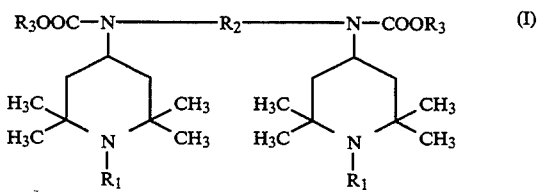

in which $R_1$ is e.g. hydrogen, $R_2$ is e.g. $C_2$-$C_{12}$alkylene and $R_3$ is e.g. $C_1$-$C_{18}$alkyl;

which process comprises reacting, in water, in the absence of an organic solvent, a compound of the formula (II)

$$Cl-COOR_3 \quad (II)$$

wherein $R_3$ is as defined above with a compound of the formula (III)

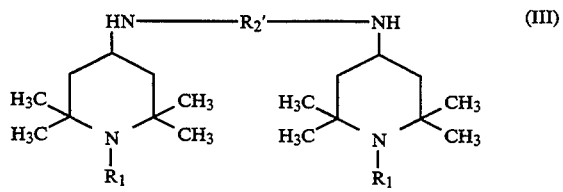

where $R_1$ is e.g. as defined above and $R_2'$ is e.g. as defined above for $R_2$, at a temperature of from 0° to 60° C., 1 to 1.5 mol of the compound of the formula (II) being used per mol —NH— group in the compound of the formula (III); and neutralizing the hydrochloric acid formed with an inorganic base.

14 Claims, No Drawings

PROCESS FOR PREPARING N,N'-BIS(HYDROCARBYLOXYCARBONYL)-N,N'-BIS(2,2,6,6-TETRAMETHYL-4-PIPERIDYL)DIAMINES

This application is a continuation of application Ser. No. 07/986,326, filed Dec. 7, 1992, now abandoned.

The present invention relates to a novel and convenient process for preparing N,N'-bis(hydrocarbyloxycarbonyl)-N,N'-bis(2,2,6,6-tetramethyl-4-piperidyl)-diamines which can be used as light stabilisers, heat stabilisers and oxidation stabilisers for synthetic polymers.

A method for the preparation of these compounds is already known and involves the use of organic solvents as the reaction medium.

Thus, U.S. Pat. No. 4,695,599 describes, for example, the preparation of N,N'-bis(ethoxycarbonyl)-N,N'-bis(2,2,6,6-tetramethyl-4-piperidyl)-1,6-hexanediamine and the use thereof as stabiliser for synthetic polymers. The preparation of this compound is carried out by reacting ethyl chlorocarbonate with N,N'-bis(2,2,6,6-tetramethyl-4-piperidyl)-1,6-hexanediamine, using 1,2-dichloroethane as the solvent in the presence of aqueous sodium hydroxide. The resulting product is purified by crystallisation from octane.

The preparation of the same compound, starting from the same reagents indicated above, is also indicated schematically in U.S. Pat. No. 4,369,321, using toluene as the reaction medium. In this case again, the resulting product is crystallised from octane.

The preparation of N,N'-bis(hydrocarbyloxycarbonyl)-N,N'-bis(2,2,6,6-tetramethyl-4-piperidyl)diamines, carried out in organic solvents, always gives coloured products, which can sometimes be used directly as intermediates for subsequent reactions, but not as stabilisers for synthetic polymers, to which they would impart an undesired coloration. Therefore, for this application, purification treatments such as crystallisation are particularly necessary, which inevitably lead to a certain reduction in the yield of useful products and, therefore, to unacceptable productions costs. Moreover, the use of organic solvents entails other disadvantages, such as a fire risk and toxicological problems.

For these reasons, the processes of the known state of the art are unsuitable for the large-scale industrial production of N,N'-bis(hydrocarbyloxycarbonyl)-N,N'-bis(2,2,6,6-tetramethyl-4-piperidyl)diamines suitable for use as stabilisers for synthetic polymers.

It has now been found that the reaction of N,N'-bis(2,2,6,6-tetramethyl-4-piperidyl)diamines with hydrocarbyl chlorocarbonates for the preparation of N,N'-bis(hydrocarbyloxycarbonyl)N,N'-bis(2,2,66-tetramethyl-4-piperidyl)diamines can easily be carried out using water as the reaction medium, in the absence of organic solvents, to give a product of high purity and very light colour, which can be used directly as stabilisers for synthetic polymers without any need for subsequent purification treatments.

The yields of the products thus prepared are significantly higher as compared with those obtained by operation in an organic solvent.

Consequently, the process of the present invention turns out to be much more advantageous than the known state of the art with respect to both a marked reduction in production costs and better protection of the environment due to the complete elimination of organic solvents.

A further advantage derives from the possibility of using coloured N,N'-bis(2,2,6,6-tetramethyl-4-piperidyl)diamines as reactants, because the impurities which cause the colour remain dissolved in the mother liquors and are easily removed by filtration and washing with water of the precipitates formed, white and directly useable products also being obtained in this case.

Therefore, the process of the present invention is very suitable for the industrial production of N,N'-bis(hydrocarbyloxycarbonyl)-N,N'-bis(2,2,6,6-tetramethyl-4-piperidyl)diamines suitable for use as stabilisers for synthetic polymers.

The present invention relates to an improved process for preparing compounds of the formula (I)

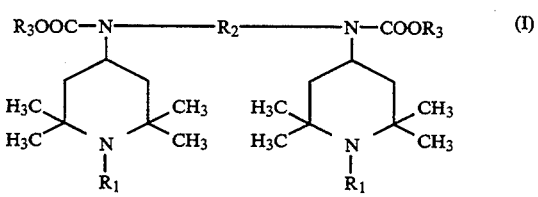

in which $R_1$ is hydrogen, $C_1$–$C_8$alkyl, $C_7$–$C_9$phenylalkyl which is unsubstituted or mono-, di- or tri-substituted on the phenyl by $C_1$–$C_4$alkyl; or $C_1$–$C_8$acyl, $R_2$ is $C_2$–$C_{12}$alkylene, $C_4$–$C_{12}$alkylene interrupted by 1, 2 or 3 oxygen atoms or by 1, 2 or 3 >N—COOR$_3$ or >N—CH$_3$ groups; $C_5$–$C_7$cycloalkylene which is unsubstituted or monosubstituted by $C_1$–$C_4$alkyl; $C_5$–$C_7$cycloalkylenedi($C_1$–$C_4$alkylene), $C_1$–$C_4$alkylenedi($C_5$–$C_7$cycloalkylene), phenylenedi($C_1$–$C_4$alkylene), or ($C_1$–$C_4$alkylene)diphenylene and $R_3$ is $C_1$–$C_{18}$alkyl, $C_3$–$C_{18}$alkyl interrupted by 1 or 2 oxygen atoms; $C_5$–$C_{12}$cycloalkyl which is unsubstituted or mono-, di- or tri-substituted by $C_1$–$C_4$alkyl; $C_3$–$C_{18}$alkenyl, phenyl which is unsubstituted or mono-, di- or tri-substituted by $C_1$–$C_4$alkyl or by $C_1$–$C_4$alkoxy; $C_7$–$C_9$phenylalkyl which is unsubstituted or mono-, di- or tri-substituted on the phenyl by $C_1$–$C_4$alkyl;

which process comprises reacting, in water, in the absence of an organic solvent, a compound of the formula (II)

wherein $R_3$ is as defined above with a compound of the formula (III)

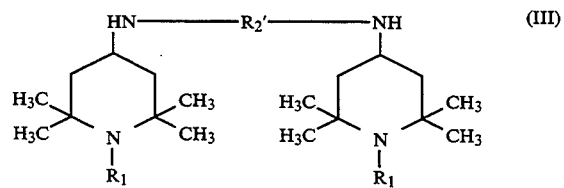

where $R_1$ is as defined above and $R_2'$ is as defined above for $R_2$ with the proviso that, if $R_2$ is $C_4$–$C_{12}$alkylene interrupted by 1, 2 or 3 >N—COOR$_3$ groups, $R_2'$ is $C_4$–$C_{12}$alkylene interrupted by 1, 2 or 3 —NH— groups, at a temperature of from 0° to 60° C., 1 to 1.5 mol of the compound of the formula (II) being used per mol —NH— group in the compound of the formula (III); and neutralising the hydrochloric acid formed with an inorganic base.

Examples of alkyl having not more than 18 carbon atoms are methyl, ethyl, propyl, isopropyl, butyl, 2-butyl, isobutyl, t-butyl, pentyl, 2-pentyl, hexyl, heptyl, octyl, 2-ethylhexyl, nonyl, decyl, undecyl, dodecyl, h-decyl, tetradecyl, hexadecyl and octadecyl.

Examples of $C_3-C_{18}$alkyl interrupted by 1 or 2 oxygen atoms are 3-oxabutyl, 3-oxapentyl, 3-oxahexyl, 3-oxaheptyl, 3-oxaundecyl, 3-oxapentadecyl, 3,6-dioxaheptyl, 3,6-dioxaoctyl and 3,6-dioxadecyl.

Examples of $C_3-C_{18}$alkenyl are allyl, 2-methylallyl, butenyl, hexenyl, undecenyl and olelyl. Allyl is preferred.

Examples of unsubstituted or substituted cycloalkyl are cyclopentyl, methylcyclopentyl, dimethylcyclopentyl, cyclohexyl, methylcyclohexyl, dimethylcyclohexyl, trimethylcyclohexyl, t-butylcyclohexyl, cyclooctyl, cyclodecyl and cyclododecyl.

Examples of substituted phenyl are methylphenyl, dimethylphenyl, trimethylphenyl, t-butylphenyl, di-t-butylphenyl, di-t-butylmethylphenyl, methoxyphenyl and ethoxyphenyl.

Examples of unsubstituted or substituted $C_7-C_9$phenylalkyl are benzyl, methylbenzyl, dimethylbenzyl, trimethylbenzyl, t-butylbenzyl and 2-phenylethyl. Benzyl is preferred.

Representatives examples of $C_1-C_8$acyl $R_1$ are formyl, acetyl, propionyl, butyryl, isobutyryl, pentanoyl, hexanoyl, heptanoyl and octanoyl. $C_1-C_8$alkanoyl is preferred. Acetyl is especially preferred.

Examples of $C_2-C_{12}$alkylene are ethylene, propylene, trimethylene, tetramethylene, pentamethylene, 2,2-dimethyltrimethylene, hexamethylene, trimethylhexamethylene, octamethylene, decamethylene and dodecamethylene.

Representative examples of $C_4-C_{12}$alkylene $R_2$ interrupted by 1, 2 or 3 oxygen atoms are 3-oxapentane-1,5-diyl, 4-oxaheptane-1,7-diyl, 3,6-dioxaoctane-1,8-diyl, 4,7-dioxadecane-1,10-diyl, 4,9-dioxadodecane-1,12-diyl, 3,6,9-trioxaundecane-1,11-diyl and 4,7,10-trioxatridecane-1,13-diyl.

Representative examples of $C_4-C_{12}$alkylene $R_2$ interrupted by 1, 2 or 3 $>N-COOR_3$ or $>N-CH_3$ groups are the groups

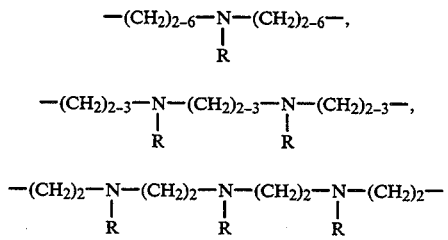

where R is $-COOR_3$ or $-CH_3$.

Representative examples of $C_4-C_{12}$alkylene $R_2'$ interrupted by 1, 2 or 3 $-NH-$ groups are the groups shown above for R with $R_2$ being hydrogen.

Representative examples of a $C_5-C_7$cycloalkylene group or substituted $C_5-C_7$cycloalkylene group $R_2$ are cyclohexylene or methylcyclohexylene.

A representative example of $C_5-C_7$cycloalkylenedi($C_1-C_4$alkylene) is cyclohexylenedimethylene and a representative example of $C_1-C_4$alkylenedi($C_5-C_7$cycloalkylene) is methylenedicyclohexylene.

A representative example of phenylenedi($C_1-C_4$alkylene) is phenylenedimethylene and a representative example of ($C_1-C_4$alkylene)diphenylene is methylenediphenylene.

The process according to the present invention is conveniently carried out by slowly adding a chlorocarbonate of the formula (II) to a solution or suspension of the compound of the formula (III) in water maintained at a temperature of from 0° to 60° C., preferably 10° to 50° C. and in particular 20° to 40° C.

In the reaction, the $-NH-$ groups which may be present in the group $R_2'$ are also converted into $>N-COOR_3$ groups.

The compounds of the formula (II) are used in a quantity of 1 to 1.5 mol, preferably 1 to 1.3 mol and in particular 1.1 to 1.2 mol, per mol $-NH-$ group in the compounds of the formula (III).

When the reaction has ended, the hydrochloric acid formed is neutralised with an inorganic base, preferably sodium or potassium hydroxide, carbonate or bicarbonate, preferably using an excess of up to 20% of theory.

This base is preferably used as an aqueous solution having a concentration of from 5 to 50%, preferably 10 to 30%.

Sodium hydroxide is the particularly preferred base.

The compounds of the formula (I) thus neutralised precipitate in the form of freely disperse solids which can easily be separated by filtration from the reaction mixture.

After washing with water and drying, the compounds of the formula (I) are obtained as powders of white colour in a yield of at least 98% of theory and in a purity, determined by gas chromatography, of at least 99%.

The quantity of water used in the reaction is not critical; nevertheless, it is preferable to use a quantity of water which is 2 to 5 times the weight of the compound of the formula (III).

The reaction time varies as a function of the reaction temperature and of the nature of the reagents used.

The course of the reaction can be followed by means of gas chromatography.

The results obtained in the preparation of the compounds of the formula (I) by the process of the present invention are highly surprising since, if the same reaction is carded out according to the procedure indicated above with compounds analogous to those of the formula (III) but not containing piperidine groups, for example with N,N'-dicyclohexyl-1,6-hexanediamine, the corresponding dicarbamates are obtained in very low yields, as a mixture with the monocarbamates and with the starting diamines. On the contrary, in this case much better results are obtained by operating in an organic solvent.

The compounds of the formulae (II) and (III), which are used according to the process of the present invention, are commercially available or can easily be prepared by known processes.

Those compounds of the formula (II) are preferred in which $R_3$ is $C_1-C_{12}$alkyl, $C_3-C_{12}$alkyl interrupted by 1 or 2 oxygen atoms; $C_3-C_{12}$alkenyl, cyclohexyl which is unsubstituted or mono-, di- or tri-substituted by $C_1-C_4$alkyl; phenyl which is unsubstituted or mono-, di- or tri-substituted by $C_1-C_4$alkyl or $C_1-C_4$alkoxy; or benzyl which is unsubstituted or mono-, di- or tri-substituted by $C_1-C_4$alkyl.

Those compounds of the formula (II) are particularly preferred in which $R_3$ is $C_1-C_8$alkyl, $C_3-C_6$alkyl interrupted by one oxygen atom; $C_3$-$C_6$alkenyl, cyclohexyl, phenyl or benzyl.

Those compounds of the formula (II) are of special interest in which $R_3$ is $C_1$-$C_6$alkyl, 3-oxabutyl, allyl, cyclohexyl or benzyl.

Those compounds of the formula (II) are of particular interest in which $R_3$ is $C_1$-$C_4$alkyl.

Those compounds of the formula (III) are preferred in which Rhd 1 is hydrogen, $C_1$-$C_4$alkyl, benzyl which is unsubstituted or mono-, di- or tri-substituted by $C_1$-$C_4$alkyl; or $C_1$-$C_4$acyl and $R_2'$ is $C_2$-$C_{10}$alkylene, $C_4$-$C_{10}$alkylene interrupted by 1, 2 or 3 oxygen atoms or by 1, 2 or 3 —NH— or >N—$CH_3$ groups; cyclohexylene, cyclohexylenedimethylene, methylenedicyclohexylene, phenylenedimethylene or methylenediphenylene.

Those compounds of the formula (III) are particularly preferred in which $R_1$ is hydrogen, methyl, benzyl or acetyl and $R_2'$ is $C_2$-$C_8$alkylene, $C_4$-$C_{10}$alkylene interrupted by 1, 2 or 3 oxygen atoms or by 1 or 2 —NH— or >N—$CH_3$ groups; cyclohexylenedimethylene, methylenedicyclohexylene or phenylenedimethylene.

Those compounds of the formula (III) are of special interest in which $R_1$ is hydrogen, methyl or acetyl and $R_2'$ is $C_2$-$C_6$alkylene, $C_6$-$C_{10}$alkylene interrupted by 2 or 3 oxygen atoms; $C_4$-$C_{10}$alkylene interrupted by 1 or 2 —NH— groups; cyclohexylenedimethylene or methylenedicyclohexylene.

Those compounds of the formula (III) are of particular interest in which $R_1$ is hydrogen and $R_2'$ is one of the groups —$(CH_2)_{2-6}$—, —$(CH_2)_3$—O—$(CH_2)_{2-4}$—O—$(CH_2)_3$— or

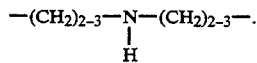

In the examples which follow, the preparation of some compounds of the formula (I) by the process of the present invention is illustrated; for comparison, the preparation of the same compounds in an organic solvent according to the known state of the art is also shown.

In addition, the preparation of N,N'-bis(methoxycarbonyl)-N,N'-dicyclohexyl-1,6-hexanediamine in water and in an organic solvent is reported.

The examples of the preparation of compounds of the formula (I) according to the present invention are given solely for illustrative purposes and do not imply any restriction.

EXAMPLE 1

Preparation of N,N'-bis(methoxycarbonyl)-N,N'-bis(2,2,6,6-tetramethyl-4-piperidyl)-1,6-hexanediamine.

83.2 g (0.88 mol) of methyl chlorocarbonate am added in 30 minutes to a solution, heated to 40° C., of 157.9 g (0.4 mol) of N,N'-bis(2,2,6,6-tetramethyl-4-piperidyl)-1,6-hexanediamine in 470 ml of water, maintaining the temperature at 40° C.

After the end of the addition, the mixture is stirred for 30 minutes at ambient temperature. A solution of 40 g (1 mol) of sodium hydroxide in 160 ml of water is then added in 30 minutes, allowing the temperature to rise up to about 50° C.

After stirring for 1 hour at ambient temperature, the precipitate obtained is separated off by filtration, washed with 200 ml of water and dried in vacuo at 70° C.

This gives 202.3 g (yield 99%) of a white powdery product of melting point 124°–125° C., having a purity of 99.5%, determined by gas chromatography. Analysis for $C_{28}H_{54}N_4O_4$ calculated: C=65.84%; H=10.66%; N=10.97% found : C=66.07%; H=10.68%; N=10.95%

Comparison A

The same compound as above is prepared as described in Example 1 of U.S. Pat. No. 4,695,599.

19.8 g (0.21 mol) of methyl chlorocarbonate are slowly added at a temperature not exceeding 0° C. to a solution, cooled to −10° C., of 39.4 g (0.1 mol) of N,N'-bis(2,2,6,6-tetramethyl-4-piperidyl)-1,6-hexanediamine in 200 ml of 1,2-dichloroethane.

A solution of 8.4 g (0.21 mol) of sodium hydroxide in 50 ml of water is then slowly added, maintaining the temperature at 0° C.

After the end of the addition, the reaction mixture is stirred for 1 hour at ambient temperature. The aqueous phase is separated off, and the organic phase is washed with water, dried over anhydrous $Na_2SO_4$ and evaporated in vacuo (22 mbar) at 70° C.

This gives 48.7 g of product as a light-yellow coloured powder melting at 123°–124° C. After crystallisation from acetone, 39.2 g (76.7% yield) of product are obtained as a white powder of melting point 124°–125° C. Carrying out the reaction in toluene instead of 1,2-dichloroethane, virtually the same result is obtained: 74.6% yield of product crystallised from acetone.

EXAMPLE 2

Preparation of N,N'-bis(methoxycarbonyl)-N,N'-bis(2,2,6,6-tetramethyl-4-piperidyl)-1,3-propanediamine.

83.2 g (0.88 mol) of methyl chlorocarbonate are reacted as described in Example 1 with 141 g (0.4 mol) of N,N'-bis(2,2,6,6-tetramethyl-4-piperidyl)-1,3-propanediamine dissolved in 420 ml of water.

This gives 185.2 g (98.8% yield) of product as a white powder of melting point 128°–128.5° C., having a purity of 99.7%, determined by gas chromatography. Analysis for $C_{25}H_{48}N_4O_4$ calculated: C=64.07%; H=10.32%; N=11.95% found : C=64.05%; H=10.34%; N=11.93%

Comparison B

The same compound as above is prepared as described for Comparison A, by reacting 19.8 g (0.21 mol) of methyl chlorocarbonate with 35.3 g (0.1 mol) of N,N'-bis(2,2,6,6-tetramethyl-4-piperidyl)-1,3-propanediamine dissolved in 200 ml of 1,2-dichloroethane.

This gives 44.8 g of product as a yellow powder melting at 127°–128° C.

After crystallisation from acetone, 35.9 g (76.6% yield) of product are obtained as a white powder of melting point 128°–128.5° C.

Carrying out the reaction in toluene instead of 1,2-dichloroethane, virtually the same result is obtained: 77% yield of product crystallised from acetone.

EXAMPLE 3

Preparation of N,N'-bis(butoxycarbonyl)-N,N'-bis(2,2,6,6-tetramethyl-4-piperidyl)-1,2-ethanediamine.

120.2 g (0.88 mol) of butyl chlorocarbonate are reacted as described in Example 1 with 135.4 g (0.4 mol) of N,N'-bis(2,2,6,6-tetramethyl-4-piperidyl)-1,2-ethanediamine dissolved in 410 ml of water.

This gives 211.6 g (98.2%) of product as a white powder of melting point 125° C., having a purity of 99.7%, determined by gas chromatography. Analysis for $C_{30}H_{58}N_4O_4$ calculated: C=66.87%; H=10.85%; N=10.40% found : C=66.85%; H=10.83%; N=10.41%

Comparison C

The same compound as above is prepared as described for Comparison A, by reacting 28.7 g (0.21 mol) of butyl chlorocarbonate with 33.8 g (0.1 mol) of N,N'-bis(2,2,6,6-tetramethyl-4-piperidyl)-1,2-ethanediamine dissolved in 200 ml of 1,2-dichloroethane.

This gives 51.4 g of product as a light-yellow, pinkish-coloured powder melting at 124°14 125° C.

After crystallisation from acetone, 42.2 g (78.3% yield) of product are obtained as a white powder of melting point 125° C.

EXAMPLE 4

Preparation of N,N'-bis(ethoxycarbonyl)-N,N'-bis(2,2,6,6-tetramethyl-4-piperidyl)-4,7-dioxa-1,10-decanediamine.

99.8 g (0.92 mol) of ethyl chlorocarbonate are reacted as described in Example 1 with 181.9 g (0.4 mol) of N,N'-bis(2,2,6,6-tetramethyl-4-piperidyl)-4,7dioxa-1,10-decanediamine dissolved in 550 ml of water.

This gives 234.8 g (98% yield) of product as a white powder of melting point 92°-93° C., having a purity of 99.4% determined by gas chromatography. Analysis for $C_{32}H_{62}N_4O_6$ calculated: C=64.18%; H=10.44%; N=9.36% found : C=64.10%; H=10.41%; N=9.38%

Comparison D

The same compound as above is prepared as described for Comparison A by reacting 22.8 g (0.21 mol) of ethyl chlorocarbonate with 45.5 g (0.1 mol) of N,N'-bis(2,2,6,6-tetramethyl-4-piperidyl)-4,7-dioxa-1,10-decanediamine dissolved in 200 ml of 1,2-dichloroethane.

This gives 58 g of product as a pinkish-yellow coloured powder of melting point 91°-92° C.

After crystallisation from hexane, 49.2 g (82.2% yield) of product are obtained as a white powder of melting point 92°-93° C.

EXAMPLE 5

Preparation of N,N',N''-tris(methoxycarbonyl)-N,N'-bis(2,2,6,6-tetramethyl-4-piperidyl)diethylenetriamine.

136.1 g (1.44 mol) of methyl chlorocarbonate are reacted as described in Example 1 with 152.7 g (0.4 mol) of N,N'-bis(2,2,6,6-tetramethyl-4-piperidyl)diethylenetriamine dissolved in 460 ml of water.

This gives 219 g (98.5% yield) of product as a white powder of melting point 103°-104° C., having a purity of 99.5% determined by gas chromatography. Analysis for $C_{28}H_{53}N_5O_6$ calculated: C=60.51%; H=9.61%; N=12.60% found : C=60.47%; H=9.55%; N=12.60%

Comparison E

The same compound as above is prepared as described for Comparison A by reacting 29.8 g (0.315 mol) of methyl chlorocarbonate with 38.2 g (0.1 mol) of N,N'-bis(2,2,6,6-tetramethyl-4-piperidyl)diethylenetriamine in 200 ml of 1,2-dichloroethane.

This gives 52.5 g of product as a pinkish-yellow coloured powder of melting point 102°-103° C.

After crystallisation from hexane, 47 g (84.6% yield) of product are obtained as a white powder of melting point 103°-104° C.

Comparison F-1

Preparation of N,N'-bis(methoxycarbonyl)-N,N'-dicyclohexyl-1,6-hexanediamine.

20.8 g (0.22 mol) of methyl chlorocarbonate are added in 30 minutes to a solution, heated to 40° C., of 28 g (0.1 mol) of N,N'-dicyclohexyl-1,6-hexanediamine in 85 ml of water.

After the end of the addition, the mixture is stirred at ambient temperature for 30 minutes.

A solution of 10 g (0.25 mol) of sodium hydroxide in 40 ml of water is then added in 30 minutes, allowing the temperature to rise to about 50° C.

After stirring for 1 hour at ambient temperature, the oil which has separated out is taken up in 40 ml of 1,2-dichloroethane; the solution obtained is washed with water, dried over anhydrous $Na_2SO_4$ and evaporated in vacuo (22 mbar) at 70° C.

This gives 30.8 g (77.7% yield) of a light yellow oil containing 55% of the desired product.

Comparison F-2

The same compound as above is prepared as described for Comparison A by reacting 19.8 g (0.21 mol) of methyl chlorocarbonate with 28 g (0.1 mol) of N,N'-dicyclohexyl-1,6-hexanediamine dissolved in 200 ml of 1,2-dichloroethane.

This gives 39 g (98.3% yield) of a reddish-yellow oil containing 98% of the desired product.

What is claimed is:

1. A process for preparing a compound of the formula (I)

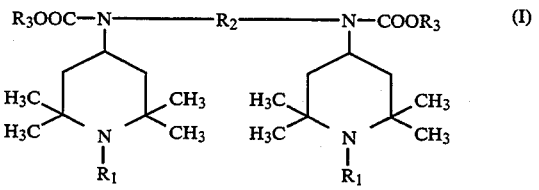

in which $R_1$ is hydrogen, $C_1$-$C_8$alkyl, $C_7$-$C_9$phenylalkyl which is unsubstituted or mono-, di- or tri-substituted on the phenyl by $C_1$-$C_4$alkyl; or $C_1$-$C_8$acyl, $R_2$ is $C_2$-$C_{12}$alkylene, $C_4$-$C_{12}$alkylene interrupted by 1, 2 or 3 oxygen atoms or by 1, 2 or 3 >N—COOR$_3$ or >N—CH$_3$ groups; $C_5$-$C_7$cycloalkylene which is unsubstituted or monosubstituted by $C_1$-$C_4$alkyl; $C_5$-$C_7$-cycloalkylenedi($C_1$-$C_4$alkylene), $C_1$-$C_4$alkylenedi($C_5$-$C_7$cycloalkylene), phenylenedi($C_1$-$C_4$alkylene), or ($C_1$-$C_4$alkylene)diphenylene and $R_3$ is $C_1$-$C_{18}$alkyl, $C_3$-$C_{18}$ alkyl interrupted by 1 or 2 oxygen atoms; $C_5$-$C_2$cycloalkyl which is unsubstituted or mono-, di- or tri-substituted by $C_1$-$C_4$alkyl; $C_3$-$C_{18}$alkenyl, phenyl which is unsubstituted or mono-, di- or tri-substituted by $C_1$-$C_4$alkyl or by $C_1$-$C_4$alkoxy; $C_7$-$C_9$phenylalkyl which is unsubstituted or mono-, di- or tri-substituted on the phenyl by $C_1$-$C_4$alkyl;

which process comprises reacting, in water, in the absence of an organic solvent, a compound of the formula (II)

$$Cl-COOR_3 \qquad (II)$$

wherein $R_3$ is as defined above with a compound of the formula (III)

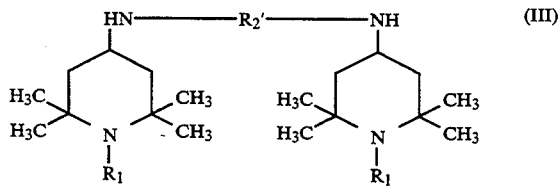

where $R_1$ is as defined above and $R_2'$ is as defined above for $R_2$ with the proviso that, if $R_2$ is $C_4$-$C_{12}$alkylene interrupted by 1, 2 or 3 >N—$COOR_3$ groups, $R_2'$ is $C_4$-$C_{12}$alkylene interrupted by 1, 2 or 3 —NH— groups, at a temperature of from 0° to 60° C., 1 to 1.5 mol of the compound of the formula (II) being used per mol —NH— group in the compound of the formula (III); and neutralising the hydrochloric acid formed with an inorganic base.

2. A process as claimed in claim 1, wherein the reaction temperature is 10° to 50° C.

3. A process according to claim 1, wherein the reaction temperature is 20° to 40° C.

4. A process according to claim 1, wherein 1 to 1.3 mol of the compound of the formula (II) are used per mol —NH— group in the compound of the formula (III).

5. A process according to claim 1, wherein 1.1 to 1.2 mol of the compound of the formula (II) are used per mol —NH— group in the compound of the formula (III).

6. A process according to claim 1, wherein a compound of the formula (II) is used in which $R_3$ is $C_1$-$C_{12}$alkyl, $C_3$-$C_{12}$alkyl interrupted by 1 or 2 oxygen atoms; $C_3$-$C_{12}$alkenyl, cyclohexyl which is unsubstituted or mono-, di- or tri-substituted by $C_1$-$C_4$alkyl; phenyl which is unsubstituted or mono-, di- or tri-substituted by $C_1$-$C_4$alkyl or $C_1$-$C_4$alkoxy; or benzyl which is unsubstituted or mono-, di- or tri-substituted by $C_1$-$C_4$alkyl.

7. A process according to claim 1, wherein a compound of the formula (II) is used in which $R_3$ is $C_1$-$C_8$alkyl, $C_3$-$C_6$alkyl interrupted by one oxygen atom; $C_3$-$C_6$alkenyl, cyclohexyl, phenyl or benzyl.

8. A process according to claim 1, wherein a compound of the formula (II) is used in which $R_3$ is $C_1$-$C_6$alkyl, 3-oxabutyl, allyl, cyclohexyl or benzyl.

9. A process according to claim 1, wherein a compound of the formula (II) is used in which $R_3$ is $C_1$-$C_4$alkyl.

10. A process according to claim 1, wherein a compound of the formula (III) is used in which $R_1$ is hydrogen, $C_1$-$C_4$alkyl, benzyl which is unsubstituted or mono-, di- or tri-substituted by $C_1$-$C_4$alkyl; or $C_1$-$C_4$acyl and $R_2'$ is $C_2$-$C_{10}$alkylene, $C_4$-$C_{10}$alkylene interrupted by 1, 2 or 3 oxygen atoms or by 1, 2 or 3 —NH— or >N—$CH_3$ groups; cyclohexylene, cyclohexylenedimethylene, methylenedicyclohexylene, phenylenedimethylene or methylenediphenylene.

11. A process according to claim 1, wherein a compound of the formula (III) is used in which $R_1$ is hydrogen, methyl, benzyl or acetyl and $R_2'$ is $C_2$-$C_8$alkylene, $C_4$-$C_{10}$alkylene interrupted by 1, 2 or 3 oxygen atoms or by 1 or 2 —NH— or >N—$CH_3$ groups; cyclohexylenedimethylene, methylenedicyclohexylene or phenylenedimethylene.

12. A process according to claim 1, wherein a compound of the formula (III) is used in which $R_1$ is hydrogen, methyl or acetyl and $R_2'$ is $C_2$-$C_6$alkylene, $C_6$-$C_{10}$alkylene interrupted by 2 or 3 oxygen atoms; $C_4$-$C_{10}$alkylene interrupted by 1 or 2 —NH— groups; cyclohexylenedimethylene or methylenedicyclohexylene.

13. A process according to claim 1, wherein a compound of the formula (III) is used in which $R_1$ is hydrogen and $R_2'$ is one of the groups —$(CH_2)_{2-6}$—,

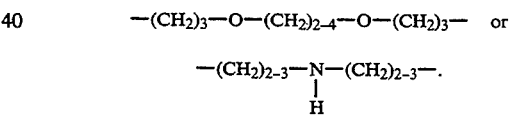

$$-(CH_2)_3-O-(CH_2)_{2-4}-O-(CH_2)_3- \quad \text{or}$$

$$-(CH_2)_{2-3}-\underset{\underset{H}{|}}{N}-(CH_2)_{2-3}-.$$

14. A process according to claim 1, wherein the inorganic base used is sodium hydroxide.

* * * * *